United States Patent
Lee et al.

(10) Patent No.: US 11,264,130 B2
(45) Date of Patent: Mar. 1, 2022

(54) SYSTEM AND METHOD FOR ESTIMATING PATHOGEN TRANSFER FROM MOBILE INTERACTION IN CLINICAL ENVIRONMENTS AND A WARNING SYSTEM AND METHOD FOR REDUCING CROSS-CONTAMINATION RISKS

(71) Applicant: FUJIFILM Business Innovation Corp., Tokyo (JP)

(72) Inventors: Matthew Len Lee, Mountain View, CA (US); Daniel Avrahami, Mountain View, CA (US); Jacob Biehl, San Jose, CA (US); Scott Carter, Menlo Park, CA (US); Kandha Sankarapandian, San Jose, CA (US)

(73) Assignee: FUJIFILM Business Innovation Corp., Tokyo (JP)

( * ) Notice: Subject to any disclaimer, the term of this patent is extended or adjusted under 35 U.S.C. 154(b) by 151 days.

(21) Appl. No.: 16/289,654

(22) Filed: Feb. 28, 2019

(65) Prior Publication Data
US 2020/0279642 A1     Sep. 3, 2020

(51) Int. Cl.
*G16H 40/40* (2018.01)
*G16H 80/00* (2018.01)
(Continued)

(52) U.S. Cl.
CPC ............ *G16H 40/40* (2018.01); *G16H 40/20* (2018.01); *G16H 40/63* (2018.01); *G16H 80/00* (2018.01)

(58) Field of Classification Search
CPC . C12Q 1/02; C12Q 1/04; G16H 40/20; G16H 40/40; G16H 40/63; G16H 80/00;
(Continued)

(56) References Cited

U.S. PATENT DOCUMENTS

| 8,525,666 | B2 * | 9/2013 | Melker | G08B 21/245 340/539.11 |
| 9,013,452 | B2 * | 4/2015 | Harrison | G06F 3/04842 345/177 |

(Continued)

OTHER PUBLICATIONS

Brady, R.R.W., et al.. Review of Mobile Communication Devices as Potential Reservoirs of Nosocomial Pathogens, Journal of Hospital Infection, 71, 2009, pp. 295-300.
(Continued)

*Primary Examiner* — Jonathan Durant
*Assistant Examiner* — Hunter J Rasnic
(74) *Attorney, Agent, or Firm* — Procopio, Cory, Hargreaves & Savitch LLP

(57) ABSTRACT

To prevent the spread of hospital-acquired infections, embodiments described herein monitor mobile device usage in clinical settings (by a physician, nurse, etc.) to characterize potential pathogenic contamination of the mobile device, the user's hands, and the surfaces in contact with the device. Our method considers the physical properties of how the device is handled and held during use, as well as the location and setting before, during, and after use to estimate potential contamination and transmission of pathogens. A system can use the estimation, along with knowledge (e.g., of the user's upcoming schedule) to alert them of potential contamination hazards and suggest when to avoid mobile device use as well as when to sanitize the device and user's hands.

21 Claims, 3 Drawing Sheets

(51) Int. Cl.
*G16H 40/63* (2018.01)
*G16H 40/20* (2018.01)

(58) Field of Classification Search
CPC ........ G16H 15/00; G16H 50/70; G16H 50/80; G16H 70/60; A61L 2202/00; A61L 2202/14; A61L 2209/00; G06Q 10/06; G08B 21/02; G08B 21/18; G08B 21/182; G08B 21/245
See application file for complete search history.

(56) References Cited

U.S. PATENT DOCUMENTS

| | | | | |
|---|---|---|---|---|
| 9,069,390 | B2* | 6/2015 | Marsden | A61L 2/28 |
| 9,778,783 | B2* | 10/2017 | Harrison | G06T 7/73 |
| 10,178,120 | B1* | 1/2019 | Keegan | H04L 63/1433 |
| 10,198,779 | B2* | 2/2019 | Pittman | H04W 4/02 |
| 10,235,861 | B1* | 3/2019 | Burns | G16H 40/63 |
| 10,275,526 | B2* | 4/2019 | Dodge | G06F 16/951 |
| 10,362,769 | B1* | 7/2019 | Kartoun | G16H 50/70 |
| 10,741,278 | B2* | 8/2020 | Sperry | G06F 3/14 |
| 10,755,369 | B2* | 8/2020 | Amarasingham | G16H 50/50 |
| 10,803,993 | B2* | 10/2020 | Huang | G16H 50/30 |
| 10,841,737 | B2* | 11/2020 | Millius | G05B 15/02 |
| 10,978,199 | B2* | 4/2021 | Boisvert | G05B 15/02 |
| 2009/0070134 | A1* | 3/2009 | Rodgers | G16H 50/80 705/2 |
| 2012/0179491 | A1* | 7/2012 | Liu | G16H 15/00 705/3 |
| 2012/0330674 | A1* | 12/2012 | Brimm | G06Q 10/10 705/2 |
| 2013/0187775 | A1* | 7/2013 | Marsden | G06F 19/00 340/540 |
| 2013/0318027 | A1* | 11/2013 | Almogy | G16H 50/80 706/52 |
| 2014/0046722 | A1* | 2/2014 | Rosenbloom | G16H 40/20 705/7.28 |
| 2014/0167917 | A2* | 6/2014 | Wallace | G16H 70/60 340/10.1 |
| 2014/0172448 | A1* | 6/2014 | Brosette | G16H 10/60 705/2 |
| 2015/0100330 | A1* | 4/2015 | Shpits | G16H 50/80 705/2 |
| 2016/0132652 | A1* | 5/2016 | Chapman Bates | G16H 50/80 706/11 |
| 2016/0171179 | A1* | 6/2016 | Donofrio | G16H 15/00 705/2 |
| 2016/0299615 | A1* | 10/2016 | Schwarz | G06F 3/04162 |
| 2017/0024531 | A1* | 1/2017 | Malaviya | G16H 40/20 |
| 2018/0308339 | A1* | 10/2018 | Marra | G08B 5/36 |
| 2019/0141914 | A1* | 5/2019 | Nelson | H04L 67/12 702/19 |
| 2019/0295725 | A1* | 9/2019 | Morrow, Jr. | G16H 70/20 |

OTHER PUBLICATIONS

Goel, M., et al., GripSense: Using Built-In Sensors to Detect Hand Posture and Pressure on Commodity Mobile Phones, UIST'12, Oct. 7-10, 2012, Cambridge, MA, pp. 545-554.

Harrison, C., et al., TapSense: Enhancing Finger Interaction on Touch Surfaces, UIST '11, Oct. 16-19, 2011, Santa Barbara, CA, 8 pgs.

Kanayama, A. K., et al., *Staphylococcus aureus* Surface Contamination of Mobile Phones and Presence of Genetically Identical Strains on the Hands of Nursing Personnel, American Journal of Infection Control, 2017, 45, pp. 929-931.

Kim, K-E, et al., Hand Grip Recognition for Mobile User Interfaces, In Proceedings of the National Conference on Artificial Intelligence, 21(2), Boston, MA, Jul. 16-20, 2006, pp. 1789-1794.

Kratz, S., et al., PointPose: Finger Pose Estimation for Touch Input on Mobile Devices Using a Depth Sensor, ITS 13, Oct. 6-9, 2013, St. Andrews, United Kingdom, 8 pgs.

Pal, S., et al., Mobile Phones: Reservoirs for the Transmission of Nosocomial Pathogens, Adv Biomed Res, Jul. 27, 2015, 4, 7 pgs.

Pillet, S., et al., Contamination of Healthcare Workers' Mobile Phones by Epidemic Viruses, Clin Microbiol Infect, 22, 2016, pp. 456.e1-456.e6.

* cited by examiner

SYSTEM AND METHOD FOR ESTIMATING PATHOGEN TRANSFER FROM MOBILE INTERACTION IN CLINICAL ENVIRONMENTS AND A WARNING SYSTEM AND METHOD FOR REDUCING CROSS-CONTAMINATION RISKS

BACKGROUND OF THE INVENTION

Technical Field

The disclosed embodiments relate in general to healthcare systems and methods and, more specifically, to a system and method for estimating pathogen transfer from mobile interaction in clinical environments and a warning system and method for reducing cross-contamination risks.

Description of the Related Art

Hand hygiene in the clinical setting not only involves proper handwashing routines but also safe habits for how to handle various objects, tools, surfaces, and devices. Health care workers (HCWs) use their hands to handle many objects that can harbor pathogenic bacteria and viruses, including their (personal) mobile phone. Surveys show that an average of 75% of HCWs report using their personal mobile devices while attending patients. Furthermore, studies have shown that 9-40% of HCWs' mobile devices have detectable virus RNA or pathogenic bacteria. Other studies have shown that the same bacteria strains are present both on nurses' hands and their mobile phones.

Health care workers, like most frequent mobile device users, are not always aware of how often they touch their phones throughout the day to perform micro-interactions such as responding to notifications, checking the time, or dismissing an incoming call. So even though HCWs may know that their personal phones can be a source or carrier of pathogens, they may not be conscious of how much contact they have with their phones.

As mobile device use has become an integral part of people's lives (and also clinical work), banning HCWs from using them is unlikely. Therefore, a solution is needed to model the risks of transferring pathogens from the phone to the HCWs hands and also to notify or warn the worker intelligently when mobile device use behaviors may result in a risky transfer of pathogens between the device and the worker's hands or a work surface.

SUMMARY OF THE INVENTION

The embodiments described herein are directed to systems and methods that substantially obviate one or more of the above and other problems associated with the conventional health care systems.

In accordance with one aspect of the embodiments described herein, there is provided a computer-implemented method, the method being performed in a system incorporating a client device comprising a central processing unit, a memory and an alerting device, the computer-implemented method involving: determining a location of the client device; classifying the determined location of the client device as a high pathogen area; detecting user interaction with the client device; and upon the detection of the user interaction with the client device, providing a warning to the user using the alerting device.

In one or more embodiments, the detected user interaction with the client device is user taking out the client device.

In one or more embodiments, the warning requests user to stop using the client device in the high pathogen area.

In one or more embodiments, the method further comprises detecting the user using the client device and upon the detection that the user used the client device, providing a second warning to the user using the alerting device.

In one or more embodiments, the second warning requests user to decontaminate the client device.

In one or more embodiments, the method further comprises detecting when the user departed the high pathogen area and, upon detection that the user departed the high pathogen area, providing a third warning to the user using the alerting device.

In one or more embodiments, the third warning requests the user to decontaminate the client device.

In one or more embodiments, the third warning requests the user to stop using the client device until it has been decontaminated.

In one or more embodiments, the method further comprises detecting when the user entered infection sensitive area and, upon detection that the user entered infection sensitive area and took out the client device, providing a fourth warning to the user using the alerting device.

In one or more embodiments, the fourth warning requests the user to stop using the client device until decontaminated.

In one or more embodiments, the method further comprises detecting when the user entered infection sensitive area and, upon detection that the user entered infection sensitive area and used the client device, providing a fifth warning to the user using the alerting device.

In one or more embodiments, the fifth warning informs the user that the infection sensitive area may have been contaminated by the client device.

In one or more embodiments, the method further comprises detecting when the user entered infection sensitive area and, upon detection that the user entered the infection sensitive area and actively used the client device, providing a sixth warning to the user using the alerting device.

In one or more embodiments, the sixth warning informs the user that the user's hands may have been contaminated by the client device.

In one or more embodiments, detecting user interaction with the client device is performed using an input characterizer and action accumulator.

In one or more embodiments, the warning is provided to the user is based on probability of transfer of pathogens between the user, the client device and the environment.

In one or more embodiments, the probability of transfer of pathogens between the user, the client device and the environment is determined by a pathogen transfer estimator.

In one or more embodiments, the probability of transfer of pathogens between the user, the client device and the environment is determined based on a contact metric.

In one or more embodiments, when the probability of transfer of pathogens between the user, the client device and the environment exceeds a predetermined risk threshold, a warning to the user is provided.

In accordance with another aspect of the embodiments described herein, there is provided a non-transitory computer-readable medium embodying a set of computer-executable instructions, which, when executed in connection with a client device incorporating a central processing unit, an alerting device and a memory, cause the client device to perform a method involving: determining a location of the client device; classifying the determined location of the client device as a high pathogen area; detecting user interaction with the client device; and upon the detection of the user interaction with the client device, providing a warning to the user using the alerting device.

In accordance with yet another aspect of the embodiments described herein, there is provided a system comprising a client device, the client device incorporating a central processing unit, an alerting device and a memory, the memory storing a set of computer-readable instructions causing the system to perform a method involving: determining a location of the client device; classifying the determined location of the client device as a high pathogen area; detecting user interaction with the client device; and upon the detection of the user interaction with the client device, providing a warning to the user using the alerting device.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive technique. Specifically.

DETAILED DESCRIPTION

In the following detailed description, reference will be made to the accompanying drawing(s), in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of a software running on a general purpose computer, in the form of a specialized hardware, or combination of software and hardware.

To prevent the spread of hospital-acquired infections, embodiments described herein monitor mobile device usage in clinical settings (by a physician, nurse, etc.) to characterize potential pathogenic contamination of the mobile device, the user's hands, and the surfaces in contact with the device. Our method considers the physical properties of how the device is handled and held during use, as well as the location and setting before, during, and after use to estimate potential contamination and transmission of pathogens. A system can use the estimation, along with knowledge (e.g., of the user's upcoming schedule) to alert them of potential contamination hazards and suggest when to avoid mobile device use as well as when to sanitize the device and user's hands.

Figure 2:
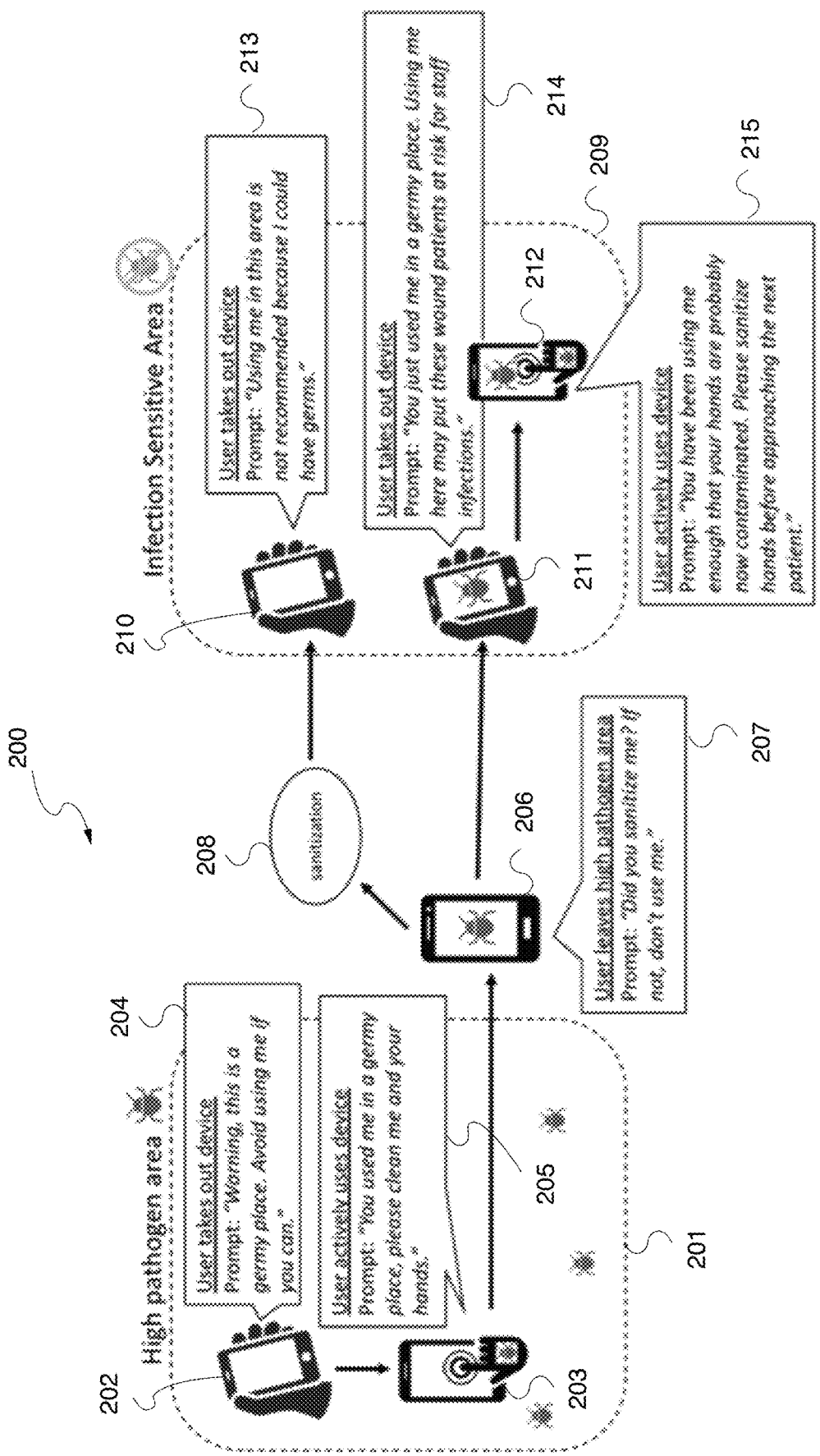
FIG. 2 illustrates an exemplary embodiment of a warning system when using in high pathogen areas (e.g., quarantine area, bedside with an infectious patient, restroom, or public waiting area) and in infection sensitive areas 209 (e.g., wound clinics, near patients with compromised immune systems, elderly, or infant).

FIG. 2 illustrates an exemplary system overview 100 showing how mobile device users interact with their device, the system characterizes each the physical properties of each input action, accumulates these actions over time, calculates a contact metric for potential contamination of the device and user's hands, and alerts the user if the risk exceeds tolerable thresholds.

Figure 1:
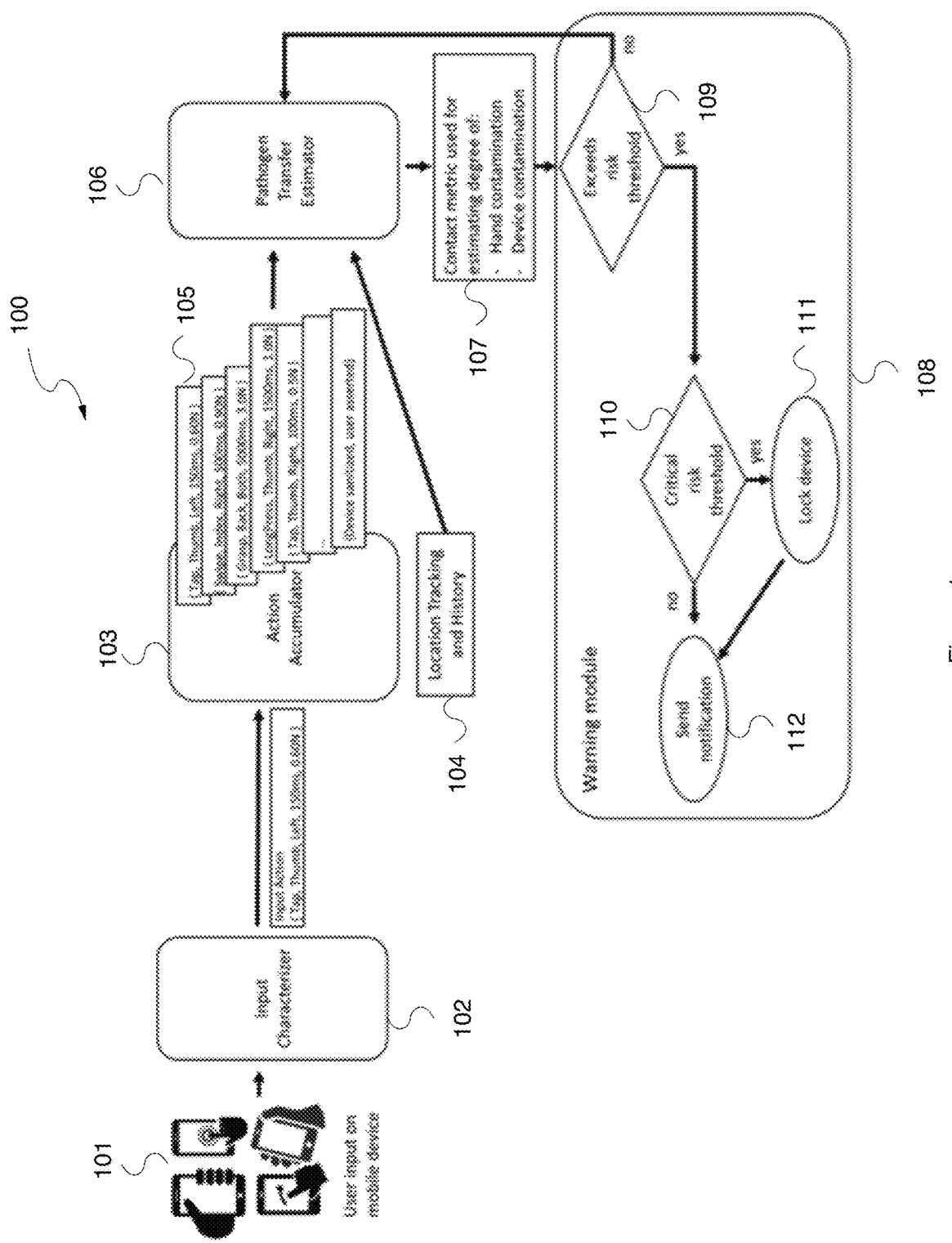
FIG. 1 illustrates an exemplary system overview 100 showing how mobile device users interact with their device, the system characterizes each the physical properties of each input action, accumulates these actions over time, calculates a contact metric for potential contamination of the device and user's hands, and alerts the user if the risk exceeds tolerable thresholds.

As shown in FIG. 1, the user provides input on mobile device 101, which is characterized by the input characterizer 102. The input characterizer 102 transmits input actions to the action accumulator 103, which produces a set of user input events 105. The set of user input events are transferred from the action accumulator to the pathogen transfer estimator 106, which uses location tracking and history information 104 from the user's mobile device for estimating pathogen transfer probability. Specifically, the pathogen transfer estimator 106 transmits a contact metric 107 used for estimating the degree of hand contamination and degree of device contamination. At block 109 of the warning module 108, the determined risk of contamination is checked against a predetermined threshold. If the threshold is exceeded, the system determined at block 110 whether critical risk threshold has been exceeded. If yes, the user's mobile device 101 is locked. Notification to user is sent in step 112.

A. Pathogen Transfer Estimation Based on User Interactions and Context

First, a brief background about how pathogens are transferred: The amount of pathogens transferred between an object and a hand is governed by a number of physical factors. Transfer efficiency increases as the following factors increase:

duration of contact
frequency of contact
pressure exerted between the finger/hand and object surface
amount of friction
how non-porous the object is
moisture level at the point(s) of contact In one or more embodiments, many of these factors can be automatically sensed and quantified based on the user's interactions with their mobile device. Mobile devices already have hardware that rely on touch/pressure interactions, so devices can be instrumented with software that analyses the user's touch interactions to model/predict the potential transfer of pathogens between the device and the user's hands.

Features from Hand Interaction

For example, the system can keep track of the duration of contact across one or more touch gestures for a cumulative duration x frequency "contact metric". Furthermore, the pressure (using pressure sensing e.g., Apple 3D touch) of each touch gesture can also be analyzed and added to the previous cumulative contact metric. Certain gestures, such as swiping and dragging, involve gliding the finger and exerting friction across the phone's surface. These input gestures can also increase the efficiency of pathogen transfer and contribute to the contact metric. The system can also adjust the contact metric based on static qualities of the phone (such as the porosity of the phone's screen and case) and also dynamic qualities of the environment such as ambient humidity.

In one or more embodiments, additional gestures can be detected that indicate the device has been sanitized, for example, wiping a cleaning cloth across the screen in a standard motion with the correct amount of pressure, coverage, and duration. Similarly, the system can use optical sensors to detect when it is placed under ultraviolet-C light with adequate intensity, frequency, and duration to be sanitized. After a detected sanitation event, the contact metric can be reset to lower level to correspond to the lower level of contamination on the device. The time since the previous sanitation event can also be used a factor in the contact metric, for example, increasing the risk of contamination as the time since the previous sanitation event increases. The system can also log each sanitation event useful for subsequent health and safety compliance audits.

In one or more embodiments, hand features of user input can also be accounted for in the contact metric. The system can identify whether one or both hands were used in the interaction, and which hand was used to touch the screen. For example, when texting with two thumbs, the user's fingers are mostly in contact with the back of the phone, elevating the risk of transfer from the back to the fingertips but not the user's palms. The system can also identify when the phone is used by only the right or left hand (because the thumb has limited reach and is directional), and differentially elevate the risks to only the hand in contact. The system can also track when the user takes a call and holds the phone up to their ear, touching their face and hair, which increases the contact area and regions for transfer.

Contextual Features

In one or more embodiments, the system can account for the context and/or environment of device usage. For example, using location sensing, if the device was used/touched in a location with a high level of dangerous pathogens (such as a quarantine area, bedside with infectious patient, restroom, or public waiting area), the system can elevate the danger of each subsequent contact with the phone and adjust its contact metric appropriately.

In one or more embodiments, likewise, the described system can also use context and/or environment to estimate the likelihood of proactive, correct behavior. For example, the system can detect that a device remains in the health worker's pocket when in high contamination spaces. Even further, the system could detect that a device remains in the pocket of the health worker while he or she also spends a meaningful amount of time in close proximity to a hand sanitation station (sink).

In one or more embodiments, the system can use the health workers detailed schedule to aid in predicting the likelihood of contact with pathogens. For example, if the worker's schedule indicates that they came from or is currently visiting a patient with an infectious disease, the system will use this information in estimating the likelihood that pathogens will be transferred to the mobile devices during interaction. This information is also useful in determining the risk of transmission and the type of warning that should be delivered by the system (see below).

Consider the following usage scenario for calculating the contamination risk score of a device and the user's hands. The user arrives at the clinic and first sanitizes her device and hands before beginning her shift. The user then enters LocationA, a high-pathogen room with patients with infectious conditions but does not use her phone in this first location. Then she takes a break and moves to LocationB, a neutral location such as an office where she access her phone. She then moves to LocationC, a high sensitivity area with patients with compromised immune systems, and interacts with patients there and also accesses her phone look up instructions on how to adjust a machine by a patient.

a) Initial State

In one or more embodiments, when the user first arrives to the clinic, the system has no knowledge of the cleanliness of either the user's hands or device. The user is prompted to sanitize her hands and device. After sanitization is performed and either automatically sensed by the system or manually indicated by the user, the system sets the device contamination score, C_device, and hands contamination score, C_hands, to 0.05.

b) Transfer from Environment to Hands in a High Pathogen Environment

In one or more embodiments, when the user enters LocationA, a room with infectious patients, she does not use the device so the system maintains the device-contamination score C_device at 0.05 (the system can also notify the user on their watch reminding them not to touch their device). However, the system assumes the user is interacting with infectious patients. Based on its environment-to-hands estimation function $\tau\_EH$, the system raises the hand-contamination score C_hands to 0.30 after the first minute in this room, and by 0.10 every additional 10 minutes thereafter (to a maximum of 1.0). For example, after spending 41 minutes with patients in this area, the system estimates C_hands to be 0.70.

c) Contamination Transfer from Hands to Device (in Neutral Pathogen Environment)

In one or more embodiments, when the user moves to LocationB, her office desk, she takes out her phone to check messages. To continuously adjust the contamination estimates, the system considers the initial contamination estimates of hands (C_hands=0.7) and device (C_device=0.05), the duration and types of interactions with the device, the hands-to-device transfer estimation function $\tau\_HD$, and the device-to-hands transfer estimation function $\tau\_DH$. Note that in this pathogen-neutral office environment, the environment-to-hands estimation $\tau\_EH$ is set to the identity function and does not increase the C_hands and it stays at 0.7.

The transfer estimation function from Hands to Device, $\tau\_HD$, can be defined by the following two transmission rates:

Holding: For each 30 seconds that the device is held, C_device is increased by (C_hands/10).

Interacting: In addition, for each second of contact with the device screen (from a tap, swipe, or typing gesture), C_device is increased by (C_hands/10).

For example, the user holds the device for 30 second (increasing C_device by 0.07) and taps the screen 8 times, each making contact for with the screen for 0.25 seconds, totaling 2 seconds of interaction (increasing C_device further by 0.14) and then locks the device and puts it in her pocket. After this example, the C_device is updated to 0.05(+0.07+0.14)=0.26.

Consider the case where the user repeated this interaction twice, the current C_device would be 0.47 and C_hands would still be 0.7.

d) Contamination Transfer from Device to Hands (in High Sensitivity Environment).

In one or more embodiments, the transfer estimation function from Device to Hands, $\tau\_DH$, can be defined by the following two transmission rates:

Holding: For each second that the device is held, C_hands is increased by (C_device/10).

Interacting: In addition, for each second of contact with the device screen (from a tap, swipe, or typing gesture), C_hands is increased by (C_device/10).

The user next enters LocationC, a high sensitivity area with patients with compromised immune systems. She washes her hands, resulting in a C_hands of 0.05. Because she knows that using her device in this area can put patients at risk, she takes out the device from her pocket and places it in a basket by the entrance. The device detects that it was taken out of a pocket and placed on a surface. Contact between the hands and device lasted 1 second.

In one or more embodiments, based on $\tau\_DH$, holding the phone briefly results in a modest transfer of pathogens (0.47/10=0.047) to the hands, increasing the C_hands to 0.10. (Notice how one short contact between the hand and device does not dramatically increase the risk of contamination from the device to hands, as is consistent with existing transmission models). The hand-contamination score C_hands is continuously adjusted using the environment-to-hands estimation function $\tau\_EH$ for this particular space, which would be low. A few moments later, the user needs to access her device to look up instructions on how to adjust a machine for patient care. The user retrieves her device and unlocks it. She holds the phone for 30 seconds while tapping 8 times (0.25 s each) and swiping 4 times (0.5 s each) (with total contact time of 4 seconds). Based on this high amount of contact with a moderately contaminated device and $\tau\_HD$, the transfer estimation function from Hands to Device, the updated C_hands now exceeds a threshold and the user is notified that her hands and device are now contaminated and pose a high risk to patients. The user can then either avoid contact with sensitive surfaces, wear gloves, or wash her hands before further work.

Machine Learning of Transfer-Estimation Functions

In one or more embodiments, the use of 4 key pathogen transfer-estimation functions is implemented: Environment-to-Hand(s) ($\tau\_EH$), Environment-to-Device ($\tau\_ED$), Hand(s)-to-Device ($\tau\_HD$), and Device-to-Hand(s) ($\tau\_DH$).

In one implementation, these functions can be learned through a supervised-learning approach. For example, first, pathogen level samples are taken from the environments of interest as well as from the user's hands and device. Then a user will perform a range of relevant actions (e.g., interact with a patient). Then pathogen readings from the user's hands and device will be taken again. The difference in readings before and after the actions is what the machine-learning model will learn to estimate. This data will be used to train the machine-learning model.

Similarly, models can be trained to estimate the transfer of pathogens from the hands to the device and from the device to the user's hands. During model training, data will be collected with various initial states of pathogens on device and hands. Data are then recorded of the user interacting with the device using different gestures, grips, and for different durations. Then, new pathogen samples are taken. The data can then be used to estimate the transfer rate based on the duration and types of interactions given initial pathogen readings of the hands and device.

B. Work Surface Contamination Detection and Tagging

Mobile devices not only pose a risk to the hands that hold them but also the surfaces that user's place them on. Work surfaces like work tables, instrument trays, beds, or other surfaces where contaminated items might be placed are all sensitive areas where a health care worker might set down their device. In these situations, there is a risk of pathogen transmission between the surface and mobile device. A similar contact model between the surface and device (that includes contact duration, frequency of contact, porosity of surface, and the prior pathogen estimate of the device or surface) can be developed and used to estimate the transmission risk.

In one or more embodiments, the mobile device can be programmed to detect (based on accelerometer or camera data) when it is set down and when it is picked back up by the user. When the device is picked back up, the camera can be used to take a photo or video of the surface it was placed on. The photo or video can be used to identify the particular surface and tag that surface as potentially contaminated from by the device or. vice versa, tag the phone as potentially contaminated by the surface. The device can also provide just-in-time prompts to the user to sanitize the surface that the device was just placed on or assert that the surface or phone is clean or safe.

In one or more embodiments, as portable devices, mobile devices need to be carried from one location to the next, often in user's hands, pockets, or bags. If the device has been determined to have been used in a high pathogen area or proximate to patient care, subsequent contact with pockets or bags could lead to contamination of these carriers. The mobile device can detect if it is placed or carried in a pocket and notify the user that the pocket might now be contaminated. A contact metric (including friction and motion) can be used to predict how much transfer has occurred between the device and pocket.

C. Alerting Users of Mobile Device Usage in High Risk or Sensitive Areas

As mentioned above, mobile devices can be used in many different settings in the clinical environment. Using the device in high pathogen environments such as a quarantine area, bedside with an infectious patient, restroom, or public waiting area can result in contamination of the mobile device.

FIG. 2 illustrates an exemplary embodiment of a warning system 200 when using in high pathogen areas 201 (e.g., quarantine area, bedside with an infectious patient, restroom, or public waiting area) and in infection sensitive areas 209 (e.g., wound clinics, near patients with compromised immune systems, elderly, or infant).

In one or more embodiments, the mobile device 202 (in conjunction with radio beacons or other proximity devices) can detect when the user takes out or handles the phone in these environments 203 and warn the user immediately of the risks for contamination and deter unnecessary use, see warnings 204 and 205.

In one or more embodiments, the device 202 can detect continued interactions with the device and then warn the user once they have left the high pathogen environment that the device is contaminated and must not be used in in sensitive areas where risk of transfer from the device to hands to environment is high unless the device is sanitized see warnings 207.

In one or more embodiments, the device (210, 211 212) can also detect when it is used in highly sensitive areas such as wound clinics 209, near patients with compromised immune systems, elderly, or infants where pathogens need to be minimized to avoid nosocomial infections. Once intended or initial device use is detected, the system can warn the user that they may transmit pathogens into the current environment, see warnings 213, 214 and 215 in FIG. 2.

In one or more embodiments, leveraging location or proximity technologies, the system can also provide lightweight reminders for proper behavior. For example, consider the situation where a health worker uses his or her device at a nurses' station or in a break room, leaves the room, put the device in his or her pocket, and then enters a patient room. Knowing that the device has just been used and detecting the device is now in a sensitive location, the device could emit a distinctive vibration or audible tone to simply remind the health worker of the need to sanitize his or her hands.

In one or more embodiments, the device can also passively keep track of user interactions in high risk areas and provide a summary of interactions to make users more aware of how often they handle their devices as an end-of-day or end-of-shift summary. These summaries, similar to physical activity monitoring like with a Fitbit or Apple Watch, can provide insights for users to understand their habits in handling their personal mobile devices in the clinical setting. Summaries over days or weeks can provide the worker with a long-term view of their adherence to proper protocols over time.

D. Warning System when Pathogen Transfer Exceeds Risk Thresholds

In one or more embodiments, the system's pathogen transfer contact metric can be tuned to allow for a reasonable level of mobile phone use (necessary for getting work done) but limiting further mobile phone use or patient contact once the potential contamination level exceeds safety thresholds. Once the system has identified that sufficient contact has taken place, the mobile device can notify the user immediately that their hands and phone may be at risk for communicating pathogens putting patients and other worker in potential danger. The notification makes the user aware of the potentially hazardous situation.

In one or more embodiments, beyond supporting awareness, the system can also automatically lock out all features, prompting the user to wash their hands and/or disinfect their device. In the absence of automatic detection of handwashing and device disinfection, the user can assert on the (now clean) device with their (now clean) hands that they have followed the disinfection protocol. Alternatively, the device can prompt the user to physically bring the device to a phone-safe zone nearby a handwashing station (where the user can sanitize their hands and device) or in a lockbox away from critical areas. After asserting that hands/device have been sanitized, the device releases the lock and allows the user to carry on with using the mobile device. The detected hand sanitization events (using either location, user assertions, etc) can also be used to update/reset the contamination estimate for the user's hands to correspond to a lower level of contamination. The time since the previous hand sanitization event can also be used to increase the estimate of hand contamination, allowing the system to notify the user to wash their hands (or avoid contact with sensitive patients and surfaces) after a certain duration. These notifications and assertions can be logged in a central database to track adherence to safe mobile device usage policies for future audits of the health care facility.

It should be finally noted that the described techniques are not limited only to preventing spread and contamination by biological hazardous materials, but also to controlling the spread of any other types or hazardous substances, such as radioactive materials and highly poisonous chemicals, such as VX. Thus, the described system may be deployed in various other environments, such as R&D labs.

E. Exemplary Embodiment of a Computer System

Figure 3:
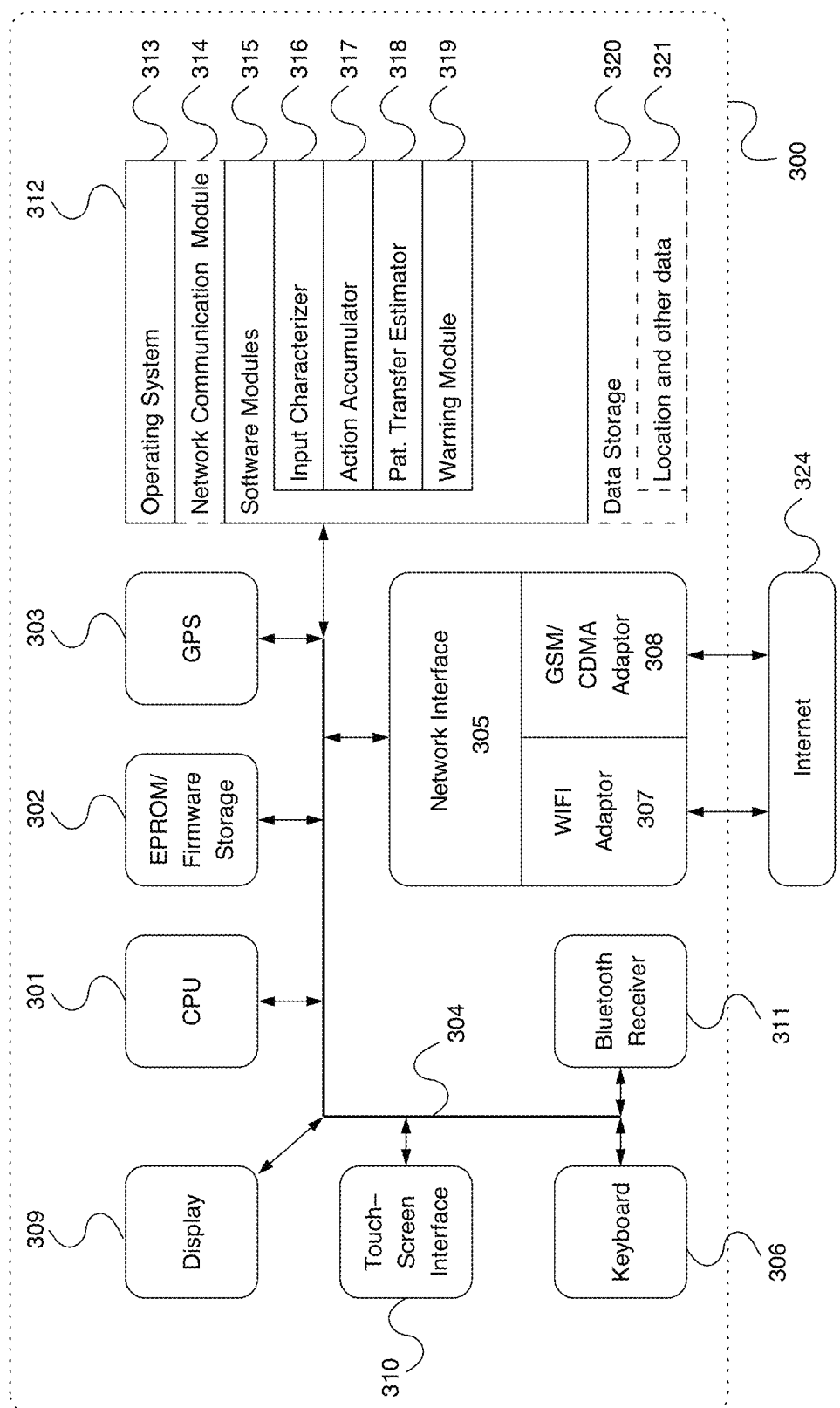
FIG. 3 illustrates an exemplary embodiment of a computer system 300, which may be used, in whole or in part, to implement the techniques described herein.

FIG. 3 illustrates an exemplary embodiment of a computer system 300, which may be used, in whole or in part, to implement the techniques described herein. In one or more embodiments, the computer 300 may be implemented within the form factor of a server, a desktop or a mobile computing device well known to persons of skill in the art. In an alternative embodiment, the computer 300 may be implemented based on a laptop or a notebook computer.

The computerized system 300 may include a data bus 304 or other interconnect or communication mechanism for communicating information across and among various hardware components of the mobile computerized system 300, and a central processing unit (CPU or simply processor) 301 coupled with the data bus 304 for processing information and performing other computational and control tasks. Computerized system 300 also includes a memory 312, such as a random access memory (RAM) or other dynamic storage device, coupled to the data bus 304 for storing various information as well as instructions to be executed by the processor 301. The memory 312 may also include persistent storage devices, such as a magnetic disk, optical disk, solid-state flash memory device or other non-volatile solid-state storage devices.

In one or more embodiments, the memory 312 may also be used for storing temporary variables or other intermediate information during execution of instructions by the processor 301. Optionally, computerized system 300 may further include a read only memory (ROM or EPROM) 302 or other static storage device coupled to the data bus 304 for storing static information and instructions for the processor 301, such as firmware necessary for the operation of the computerized system 300, basic input-output system (BIOS), as well as various configuration parameters of the computerized system 300.

In one or more embodiments, the computerized system 300 may incorporate a display (alerting) device 309, which may be also coupled to the data bus 304, for displaying various information to a user of the computerized system 300. In an alternative embodiment, the display (alerting) device 309 may be associated with a graphics controller and/or graphics processor (not shown). The display (alerting) device 309 may be implemented as a liquid crystal display (LCD), manufactured, for example, using a thin-film transistor (TFT) technology or an organic light emitting diode (OLED) technology, both of which are well known to persons of ordinary skill in the art. In various embodiments, the display (alerting) device 309 may be incorporated into the same general enclosure with the remaining components of the computerized system 300. In an alternative embodiment, the display (alerting) device 309 may be positioned outside of such enclosure. In addition, in various embodiments, the display (alerting) device 309 may also include audible and tactile/vibrational modalities to alert the user of the pathogen transfer possibility as described above.

In one or more embodiments, the computerized system 300 may further incorporate a GPS receiver 303 connected to the data bus 304 and configured to receive location information from one or more GPS satellites and transmit this information to the processor 301 via the data bus 304.

In one or more embodiments, the computerized system 300 may incorporate one or more input devices, such as a touchscreen interface 310 for receiving tactile commands and a keyboard 306, which all may be coupled to the aforesaid data bus 304 for communicating information, including, without limitation, user command selections to the processor 301. In an alternative embodiment, input devices may include a system for tracking eye movements of the user (not shown), which may be used to indicate to the computerized system 300 the command selection by the user.

In one or more embodiments, the computerized system 300 may additionally include a location signal receiver 311, such as a Bluetooth receiver, configured to perform scan for beacons 101 and supply scan data described above to the processor 301 via the data bus 304.

In one or more embodiments, the computerized system 300 may additionally include a communication interface, such as a network interface 305 coupled to the data bus 304. The network interface 305 may be configured to establish a connection between the computerized system 300 and the Internet 324 using at least one of WIFI interface 307 and the cellular network (GSM or CDMA) adaptor 308. The network interface 305 may be configured to provide a two-way data communication between the computerized system 300 and the Internet 324. The WIFI interface 307 may operate in compliance with 802.11a, 802.11b, 802.11g and/or 802.11n protocols as well as Bluetooth protocol well known to persons of ordinary skill in the art. In an exemplary implementation, the WIFI interface 307 and the cellular network (GSM or CDMA) adaptor 308 send and receive electrical or electromagnetic signals that carry digital data streams representing various types of information. For example, the aforesaid networking components may be used to establish a network data connection between the computerized system 300 and other components of the localization system 100, such as the central server 104 and third party services/applications 108.

In one or more embodiments, the Internet 324 typically provides data communication through one or more sub-networks to other network resources. Thus, the computerized system 300 is capable of accessing a variety of network resources located anywhere on the Internet 324, such as web servers, other content servers as well as other network data storage resources. In one or more embodiments, the computerized system 300 is configured send and receive messages, media and other data, including application program code, through a variety of network(s) including Internet 324 by means of the network interface 305. In the Internet example, when the computerized system 300 acts as a network client, it may request code or data for an application program executing on the computerized system 300. Similarly, it may send various data or computer code to other network resources.

In one or more embodiments, the computerized system 300 uses the network interface 305 to send request(s), via the Internet 324, such as HTTP requests, to the central server 104 and receive various information, including, without limitation, the aforesaid location information and the timestamp, therefrom.

In one or more embodiments, the functionality described herein is implemented by computerized system 300 in response to processor 301 executing one or more sequences of one or more instructions contained in the memory 312. Such instructions may be read into the memory 312 from another computer-readable medium. Execution of the sequences of instructions contained in the memory 312 causes the processor 301 to perform the various process steps described herein. In alternative embodiments, hard-wired circuitry may be used in place of or in combination with software instructions to implement the embodiments of the invention. Thus, embodiments of the invention are not limited to any specific combination of hardware circuitry and software.

The term "computer-readable medium" as used herein refers to any medium that participates in providing instructions to processor 301 for execution. The computer-readable medium is just one example of a machine-readable medium, which may carry instructions for implementing any of the methods and/or techniques described herein. Such a medium may take many forms, including but not limited to, non-volatile media and volatile media.

Common forms of non-transitory computer-readable media include, for example, a floppy disk, a flexible disk, hard disk, magnetic tape, or any other magnetic medium, a CD-ROM, any other optical medium, punchcards, paper-tape, any other physical medium with patterns of holes, a RAM, a PROM, an EPROM, a FLASH-EPROM, a flash drive, a memory card, any other memory chip or cartridge, or any other medium from which a computer can read. Various forms of computer readable media may be involved in carrying one or more sequences of one or more instructions to processor 301 for execution. For example, the instructions may initially be carried on a magnetic disk from a remote computer. Alternatively, a remote computer can load the instructions into its dynamic memory and send the instructions over the Internet 324. Specifically, the computer instructions may be downloaded into the memory 312 of the computerized system 300 from the foresaid remote computer via the Internet 324 using a variety of network data communication protocols well known in the art.

In one or more embodiments, the memory 312 of the computerized system 300 may store any of the following software programs, applications or modules:

1. Operating system (OS) 313, which may be a mobile operating system for implementing basic system services and managing various hardware components of the computerized system 300. Exemplary embodiments of the operating system 313 are well known to persons of skill in the art, and may include any now known or later developed mobile operating systems.

2. Network communication module 314 for enabling network communications using one or more network interfaces described below.

3. Software modules 315 may include, for example, a set of software applications executed by the processor 301 of the computerized system 300, which cause the computerized mobile system 300 to perform certain predetermined functions, described above, such as input characterizer 316, action accumulator 317, pathogen transfer estimator 318 and warning generation module 319.

3. Data storage 318 may be used, for example, for storing locations and other data and thresholds 319.

Finally, it should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the present invention. For example, the described software may be implemented in a wide variety of programming or scripting languages, such as Assembler, C/C++, Objective-C, perl, shell, PHP, Java, as well as any now known or later developed programming or scripting language.

Moreover, other implementations of the invention will be apparent to those skilled in the art from consideration of the specification and practice of the invention disclosed herein. Various aspects and/or components of the described embodiments may be used singly or in any combination in the system and method for estimating pathogen transfer from mobile interaction in clinical environments and a warning system and method for reducing cross-contamination risks. It is intended that the specification and examples be considered as exemplary only, with a true scope and spirit of the invention being indicated by the following claims.

What is claimed is:

1. A computer-implemented method, the method being performed in a system comprising a client device, the client device comprising a central processing unit, a memory, a location signal receiver, one or more input sensors, and an alerting device, the computer-implemented method comprising:
    determining, by the central processing unit of the client device, a location of the client device based on at least one localization signal received using the localization signal receiver of the client device;
    classifying, by the central processing unit of the client device, the determined location of the client device as a high pathogen area;
    detecting, by the central processing unit of the client device, user interactions on the client device by using the one or more input sensors of the client device to detect inputs onto the client device;
    determining, by the central processing unit of the client device, a contact metric indicative of an amount of interaction associated with the client device, the contact metric based on duration of each of the user interactions on the client device and frequency of each of the user interactions on the client device;
    determining, by the central processing unit of the client device, a probability of pathogen transfer between the user and the client device by estimating a degree of user contamination and a degree of device contamination based on the determined location and the contact metric;
    upon the determination of the probability of transfer of pathogens, determining, by the central processing unit of the client device, whether the probability of transfer of pathogens exceeds a predetermined risk threshold;
    locking the client device, by the central processing unit of the client device, based on the probability of transfer of pathogens exceeding the predetermined risk threshold; and
    when the probability of transfer of pathogens does not exceed the predetermined risk threshold, providing, by the central processing unit of the client device, a warning to the user using the alerting device of the client device,
    wherein the central processing unit of the client device is configured to execute instructions stored in the memory of the client device to perform the computer-implemented method, and
    wherein the client device is a mobile device.

2. The computer-implemented method of claim 1, wherein the detected user interactions with the client device is the user taking out the client device.

3. The computer-implemented method of claim 1, wherein the warning requests the user to stop using the client device in the high pathogen area.

4. The computer-implemented method of claim 1, further comprising detecting the use of the client device and upon the detection that the client device has been used, providing a second warning to the user using the alerting device.

5. The computer-implemented method of claim 4, wherein the second warning requests user to decontaminate the client device and sanitize hands.

6. The computer-implemented method of claim 1, further comprising detecting when the client device departed the high pathogen area and, upon detection that the client device departed the high pathogen area, providing a third warning to the user using the alerting device.

7. The computer-implemented method of claim 6, wherein the third warning requests the user to decontaminate the client device and sanitize hands.

8. The computer-implemented method of claim 6, wherein the third warning requests the user to stop using the client device until it has been decontaminated.

9. The computer-implemented method of claim 1, further comprising detecting when the client device entered infection sensitive area and, upon detection that the client device entered infection sensitive area and took out the client device, providing a fourth warning to the user using the alerting device.

10. The computer-implemented method of claim 9, wherein the fourth warning requests the user to stop using the client device until the client device has been decontaminated and the user's hands have been sanitized.

11. The computer-implemented method of claim 1, further comprising detecting when the client device entered infection sensitive area and, upon detection that the client device entered infection sensitive area and used the client device, providing a fifth warning to the user using the alerting device.

12. The computer-implemented method of claim 11, wherein the fifth warning informs the user that the infection sensitive area may have been contaminated by the client device.

13. The computer-implemented method of claim 1, further comprising detecting when the client device entered infection sensitive area and, upon detection that the client device entered the infection sensitive area and actively used the client device, providing a sixth warning to the user using the alerting device.

14. The computer-implemented method of claim 13, wherein the sixth warning informs the user that the user may have been contaminated by the client device.

15. The computer-implemented method of claim 1, wherein detecting user interactions with the client device is performed using an input characterizer and action accumulator.

16. The computer-implemented method of claim 1, wherein the probability of transfer of pathogens between the user and the client device is based on a probability of transfer of pathogens between the user and the environment.

17. The computer-implemented method of claim 1, wherein the probability of transfer of pathogens is determined by a pathogen transfer estimator.

18. The computer-implemented method of claim 1, wherein the detected user interactions comprises at least one of holding the client device and contacting a screen of the client device, wherein the contact metric is incremented for each 30 seconds the client device is held and the contact metric is incremented for each second of contact with the screen of the client device.

19. The computer-implemented method of claim 1, wherein the client device is a mobile phone.

20. A non-transitory computer-readable medium embodying a set of computer-executable instructions, which, when executed in connection with a client device comprising a central processing unit, an alerting device, a location signal receiver, one or more input sensors, and a memory, cause the client device to:

determine, by the central processing unit of the client device, a location of the client device based on at least one localization signal received using the localization signal receiver of the client device;

classify, by the central processing unit of the client device, the determined location of the client device as a high pathogen area;

detect, by the central processing unit of the client device, user interactions on the client device by using the one or more input sensors of the client device to detect inputs onto the client device;

determine, by the central processing unit of the client device, a contact metric indicative of an amount of interaction associated with the client device, the contact metric based on duration of each of the user interactions on the client device and frequency of each of the user interactions on the client device;

determine, by the central processing unit of the client device, a probability of pathogen transfer between the user and the client device by estimating a degree of user contamination and a degree of device contamination based on the determined location and the contact metric;

upon the determination of the probability of transfer of pathogens, determine, by the central processing unit of the client device, whether the probability of transfer of pathogens exceeds a predetermined risk threshold;

lock the client device, by the central processing unit of the client device, based on the probability of transfer of pathogens exceeding the predetermined risk threshold; and when the probability of transfer of pathogens does not exceed the predetermined risk threshold, provide, by the central processing unit of the client device, a warning to the user using the alerting device of the client device, wherein the client device is a mobile device.

21. A system comprising a client device, the client device comprising a central processing unit, an alerting device, a location signal receiver, one or more input sensors, and a memory, the memory storing a set of computer-readable instructions causing the client device to:

determine, by the central processing unit of the client device, a location of the client device based on at least one localization signal received using the localization signal receiver of the client device;

classify, by the central processing unit of the client device, the determined location of the client device as a high pathogen area;

detect, by the central processing unit of the client device, user interactions on the client device by using the one or more input sensors of the client device to detect inputs onto the client device;

determine, by the central processing unit of the client device, a contact metric indicative of an amount of interaction associated with the client device, the contact metric based on duration of each of the user interactions on the client device and frequency of each of the user interactions on the client device;

determine, by the central processing unit of the client device, a probability of pathogen transfer between the user and the client device by estimating a degree of user contamination and a degree of device contamination based on the determined location and the contact metric;

upon the determination of the probability of transfer of pathogens, determine, by the central processing unit of the client device, whether the probability of transfer of pathogens exceeds a predetermined risk threshold;

lock the client device, by the central processing unit of the client device, based on the probability of transfer of pathogens exceeding the predetermined risk threshold; and when the probability of transfer of pathogens does not exceed the predetermined risk threshold, provide, by the central processing unit of the client device, a warning to the user using the alerting device of the client device, wherein the client device is a mobile device.

* * * * *